(12) United States Patent
Kuan et al.

(10) Patent No.: US 8,663,582 B2
(45) Date of Patent: Mar. 4, 2014

(54) INTEGRAL-TYPE REACTION CARTRIDGE

(75) Inventors: Cheng-Chun Kuan, Xindian (TW); Wei-Sung Chen, Xindian (TW)

(73) Assignee: RBC Bioscience Corp., Taipei County (TW)

( * ) Notice: Subject to any disclaimer, the term of this patent is extended or adjusted under 35 U.S.C. 154(b) by 285 days.

(21) Appl. No.: 12/846,923

(22) Filed: Jul. 30, 2010

(65) Prior Publication Data
US 2011/0104028 A1 May 5, 2011

(30) Foreign Application Priority Data

Oct. 30, 2009 (TW) .............................. 98136822 A

(51) Int. Cl.
*A61J 1/06* (2006.01)
(52) U.S. Cl.
USPC .......................................................... 422/554
(58) Field of Classification Search
USPC .......................................................... 422/554
See application file for complete search history.

(56) References Cited

U.S. PATENT DOCUMENTS

| | | | | |
|---|---|---|---|---|
| 4,685,304 A * | 8/1987 | Essig | ................................. | 62/68 |
| 4,720,374 A * | 1/1988 | Ramachandran | ............. | 422/310 |
| 5,009,942 A * | 4/1991 | Benin et al. | ................... | 428/36.6 |
| 5,501,982 A * | 3/1996 | Saldivar et al. | ............... | 436/150 |
| 5,567,326 A * | 10/1996 | Ekenberg et al. | ............. | 210/695 |
| 5,609,822 A * | 3/1997 | Carey et al. | ..................... | 422/63 |
| 5,665,558 A * | 9/1997 | Frame et al. | ................. | 435/7.25 |
| 5,705,062 A * | 1/1998 | Knobel | ......................... | 210/205 |
| 6,425,438 B1 * | 7/2002 | Hahn | .............................. | 165/47 |
| 6,511,634 B1 * | 1/2003 | Bradshaw et al. | ............. | 422/559 |
| 6,579,453 B1 * | 6/2003 | Bachler et al. | ................ | 210/222 |
| 6,602,474 B1 * | 8/2003 | Tajima | .......................... | 422/553 |
| 2002/0155616 A1 * | 10/2002 | Hiramatsu et al. | ............ | 436/165 |
| 2003/0113235 A1 * | 6/2003 | Yokoi et al. | .................... | 422/102 |
| 2005/0271550 A1 * | 12/2005 | Talmer et al. | ................... | 422/99 |
| 2009/0129978 A1 * | 5/2009 | Wilson et al. | ................... | 422/61 |

\* cited by examiner

*Primary Examiner* — Lore Jarrett

(74) *Attorney, Agent, or Firm* — Ming Chow; Sinorica, LLC

(57) ABSTRACT

An integral-type reaction cartridge includes a plurality of reaction containers and at least a separation container. The plural reaction containers and the separation container are integrally formed of plastic and lined along a first direction. The separation container has a first end, a second end opposing the first end, and a hollow accommodating space between the first and second ends, wherein the first end is an open end, the second end is a closed end, and the accommodating space tapers from the first end to the second end. The accommodating space has a first side and a second side along the first direction, as well as a third side and a fourth side along a second direction perpendicular to the first direction. Near the second end, at least one of the first side and the second side has a greater slope than the third side and the fourth side.

3 Claims, 8 Drawing Sheets

INTEGRAL-TYPE REACTION CARTRIDGE

BACKGROUND OF THE INVENTION

1. Technical Field

The present invention relates to an integral-type reaction cartridge and, more particularly, to an integral-type reaction cartridge for separating a target substance.

2. Description of Related Art

Nowadays, it is a trend to use magnetic separation in the purification and isolation of biomolecules. Based on the attractability of magnetic particles to magnetic fields, the magnetic separation technique can be used to separate a target substance bound to magnetic particles from a complex and highly viscous mixture and is applicable to bio-affinity adsorption, protein or nucleic acid isolation, cell marking and classification, immunochemistry, and so on. The most significant advantage of magnetic separation is the efficiency with which a target substance can be extracted at high purity. More specifically, the target substance can be eluted from the purification device as soon as the magnetic field is removed. In contrast to the conventional separation techniques such as centrifugation, filtering, and chromatography which are more complicated and typically require multiple uses of chemicals, magnetic separation shows a lower risk of damaging the target substance during purification and therefore is more capable of preserving the activity of the target substance.

Take a genetic analysis of a target substance for example. The target substance, a solution, and magnetic particles are placed in a reaction container of a reaction cartridge for reaction such that the target substance is bound to the magnetic particles. Afterward, the mixture is transferred to a separation container of the reaction cartridge by a drawing mechanism. When a magnetic field is subsequently applied to the separation container from the outside, the target substance and the magnetic particles are attracted to the wall of the separation container in a concentrated manner. Then, a drawing mechanism is placed in the separation container to draw out the non-target substance, which is not bound to the magnetic particles, and the magnetic field is removed. Thus, only the target substance-bound magnetic particles are left in the separation container. However, if the drawing mechanism is improperly positioned in the separation container during the drawing process, the target substance and the magnetic particles are likely to be drawn out, too, thereby reducing the accuracy of the test result. While the drawing mechanism can be improved upon to solve the foregoing problem, the improvement process is complicated and time-consuming. Therefore, it is an important issue in the related industry to find an alternative way to increase the accuracy of test results while lowering the costs of tests.

BRIEF SUMMARY OF THE INVENTION

To overcome the aforesaid drawback of the prior art, the present invention provides an integral-type reaction cartridge including a plurality of reaction containers and at least one separation container. The plurality of reaction containers and the at least one separation container are integrally formed of plastic and lined along a first direction. Each separation container has a first end, a second end opposing the first end, and a hollow accommodating space between the first end and the second end, wherein the first end is an open end, the second end is a closed end, and the accommodating space tapers from the first end to the second end. Each accommodating space has a first side and a second side along the first direction. Each accommodating space further has a third side and a fourth side along a second direction perpendicular to the first direction. Near the second end of each separation container, at least one of the first side and the second side of the corresponding accommodating space has a lesser slope than the corresponding third and fourth sides.

The present invention also provides an integral-type reaction cartridge including a plurality of reaction containers and two separation containers. The plurality of reaction containers and the two separation containers are integrally formed of plastic and lined along a first direction. The two separation containers are adjacent to each other and each have a first end, a second end opposing the first end, and a hollow accommodating space between the first end and the second end, wherein the first end is an open end, the second end is a closed end, and the accommodating space tapers from the first end to the second end. Near the second ends, each of the adjacent sides of the two separation containers located along a first direction has a lesser slope than the sides of the corresponding accommodating space that are located along a second direction, wherein the second direction is perpendicular to the first direction.

The primary object of the present invention is to provide an integral-type reaction cartridge whose at least one separation container is configured to prevent magnetic particles contained therein and a target substance bound to the magnetic particles from being drawn out mistakenly by a drawing mechanism.

It is another object of the present invention to provide an integral-type reaction cartridge whose at least one separation container is configured to increase the purity of the final product.

BRIEF DESCRIPTION OF THE SEVERAL VIEWS OF THE DRAWINGS

The invention as well as a preferred mode of use, further objects, and advantages thereof will be best understood by referring to the following detailed description of the preferred embodiments in conjunction with the accompanying drawings, in which.

DETAILED DESCRIPTION OF THE INVENTION

The present invention provides an integral-type reaction cartridge in which the biomolecule purification principle employed is well known to a person of ordinary skill in the art and therefore is not detailed herein. Besides, it is to be understood that the drawings referred to in the following description are intended to demonstrate the features of the present invention only schematically and hence are not necessarily drawn to scale.

Figure 1A:
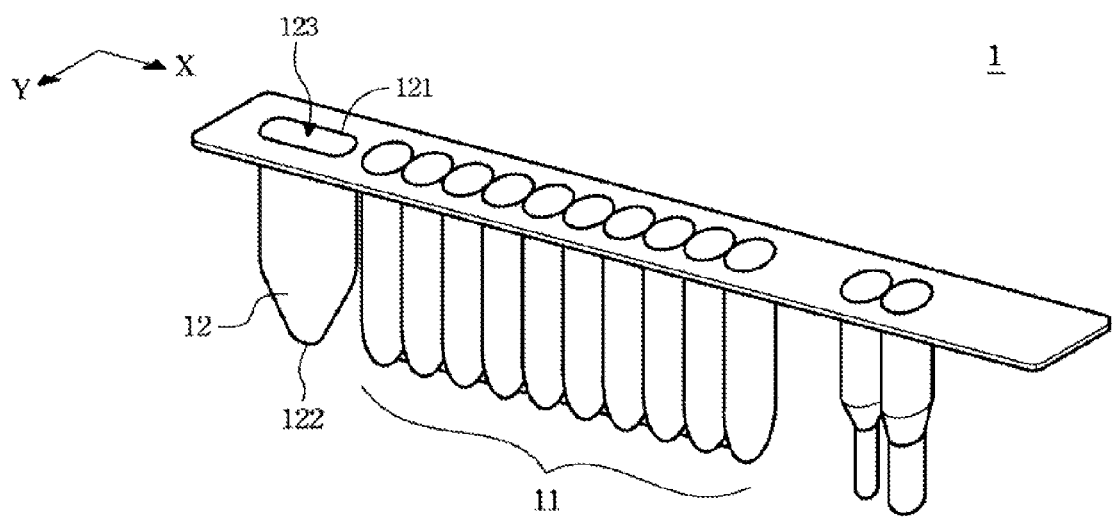
FIG. 1A is a perspective view of an integral-type reaction cartridge according to a first preferred embodiment of the present invention.

Referring to FIG. 1A for an integral-type reaction cartridge 1 according to the first preferred embodiment of the present invention, the integral-type reaction cartridge 1 includes a plurality of reaction containers 11 and a separation container 12. The reaction containers 11 and the separation container 12 are integrally formed of plastic and lined along a first direction X.

Figure 1B:
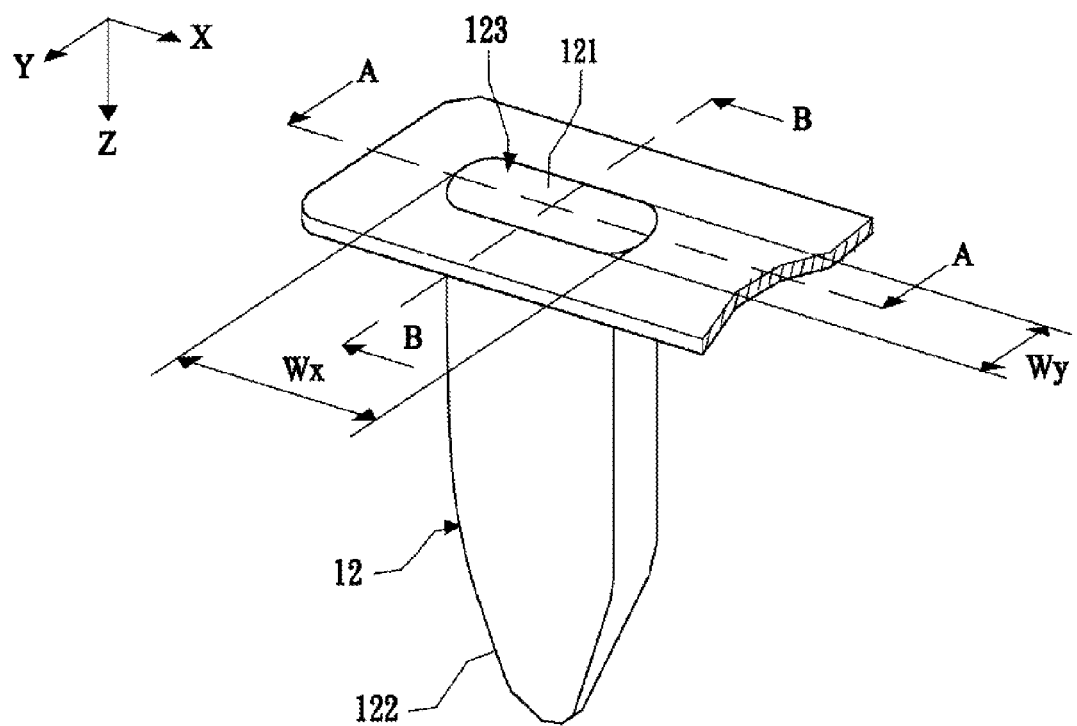
FIG. 1B is a perspective view of a separation container of the integral-type reaction cartridge shown in FIG. 1A.

As shown in FIG. 1B, the separation container 12 has a first end 121 and a second end 122 opposing the first end 121, wherein the first end 121 is an open end, and the second end 122 is a closed end. The separation container 12 further has a hollow accommodating space 123 between the first end 121 and the second end 122.

Figure 1C:
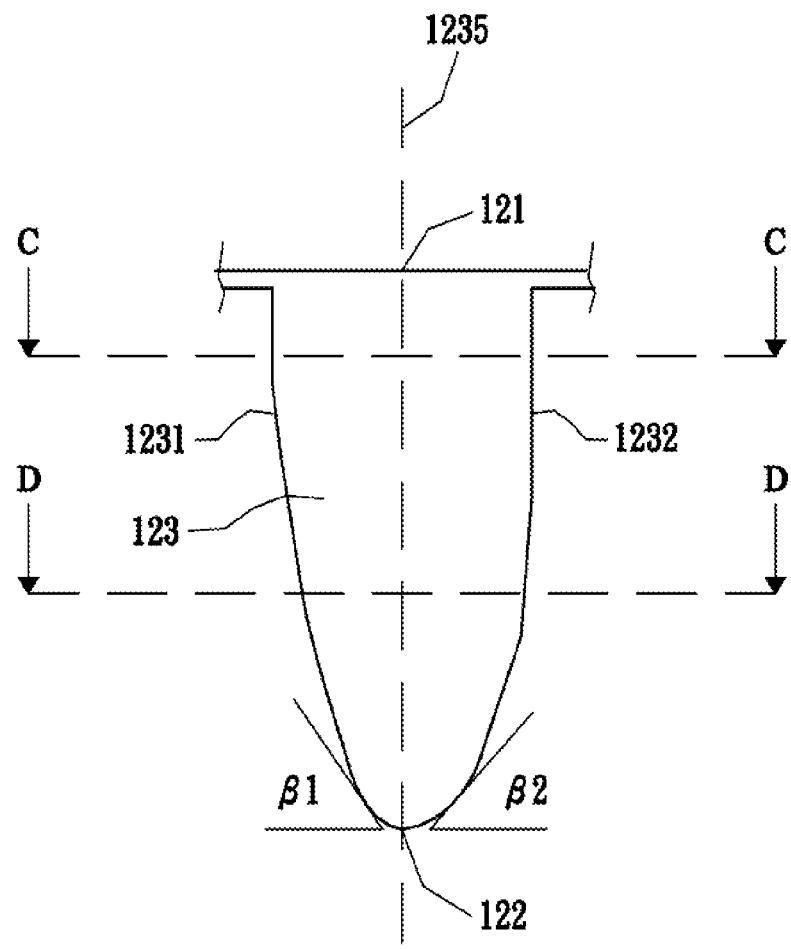
FIG. 1C is a sectional view of the separation container shown in FIG. 1B along a first direction.
Figure 1D:
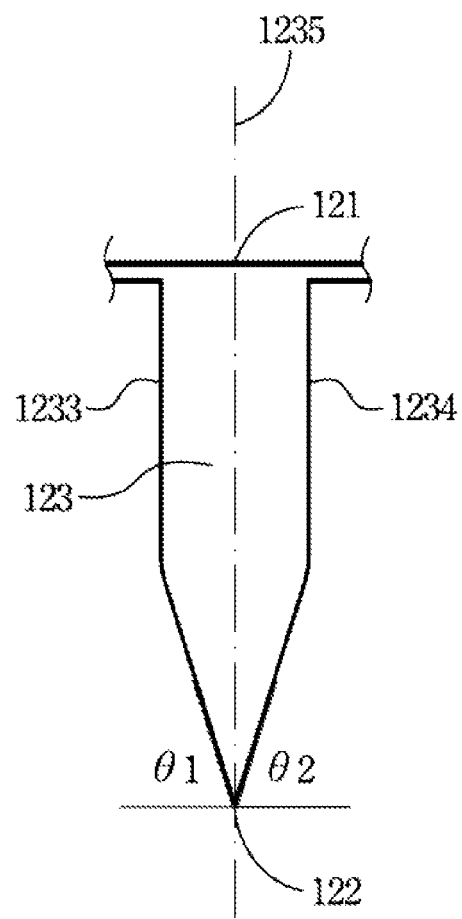
FIG. 1D is a sectional view of the separation container shown in FIG. 1B along a second direction.

FIG. 1C is a sectional view of the separation container 12 taken along line A-A of FIG. 1B, wherein line A-A is parallel to the first direction X. As shown in the drawing, the accommodating space 123 has a first side 1231 and a second side 1232 along the first direction X. Both the first side 1231 and the second side 1232 curve toward a central axis 1235 of the accommodating space 123, with the first side 1231 having a slope β1, and the second side 1232 having a slope β2. Referring to FIG. 1D for a sectional view of the separation container 12 taken along line B-B of FIG. 1B, wherein line B-B is parallel to a second direction Y, the accommodating space 123 has a third side 1233 and a fourth side 1234 along the second direction Y. The third side 1233 and the fourth side 1234 also curve toward the central axis 1235 of the accommodating space 123, with the third side 1233 having a slope θ1, and the fourth side 1234 having a slope θ2. The slope θ1 of the third side 1233 or the slope θ2 of the fourth side 1234 is greater than the slope β1 of the first side 1231 and the slope β2 of the second side 1232; in other words, θ1>β1 and θ1>β2, or θ2>β1 and θ2>β2. While the slope θ1 of the third side 1233 is shown in FIG. 1C as greater than the slope β1 of the first side 1231 and the slope β2 of the second side 1232, it should be understood by a person of ordinary skill in the art that an equivalent substitution is to make the slope θ2 of the fourth side 1234 greater than the slope β1 of the first side 1231 and the slope β2 of the second side 1232.

Figure 1E:
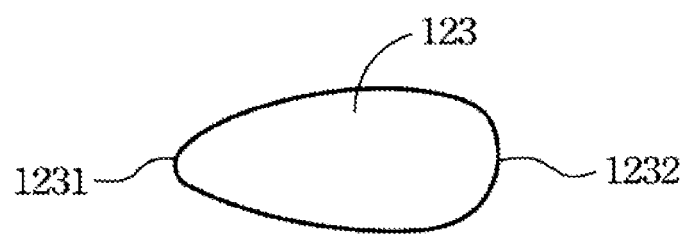
FIG. 1E is a sectional view of the separation container shown in FIG. 1B along line C-C of FIG. 1C.
Figure 1F:
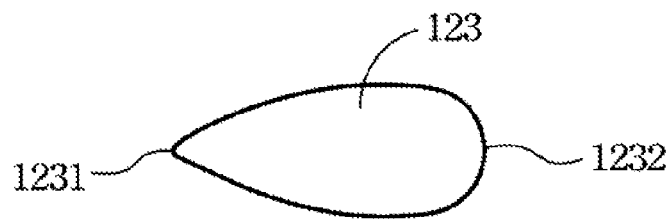
FIG. 1F is a sectional view of the separation container shown in FIG. 1B along line D-D of FIG. 1C.

Based on the foregoing design, the accommodating space 123 of the separation container 12 tapers from the first end 121 to the second end 122. In addition, the first side 1231 of the accommodating space 123 of the separation container 12 changes its configuration along a third direction Z which is perpendicular to the first direction X and the second direction Y. More specifically, the first side 1231 changes from a curved configuration near the first end 121 to a pointed configuration near the second end 122, as can be seen more clearly in FIG. 1E and FIG. 1F, which are sectional views of the separation container 12 along lines C-C and D-D respectively. Referring to FIG. 1E, the first side 1231 of the accommodating space 123 has a curved configuration near the first end 121. However, referring to FIG. 1F, which is a sectional view of the separation container 12 near the second end 122, the first side 1231 has a pointed configuration near the second end 122 of the separation container 12 due to the fact that not only do all of the first through fourth sides 1231, 1232, 1233, 1234 of the accommodating space 123 curve toward the central axis 1235 of the accommodating space 123, but also the slope θ1 of the third side 1233 is greater than the slope β1 of the first side 1231 and the slope β2 of the second side 1232, as stated previously with reference to FIGS. 1C and 1D.

Figure 1G:
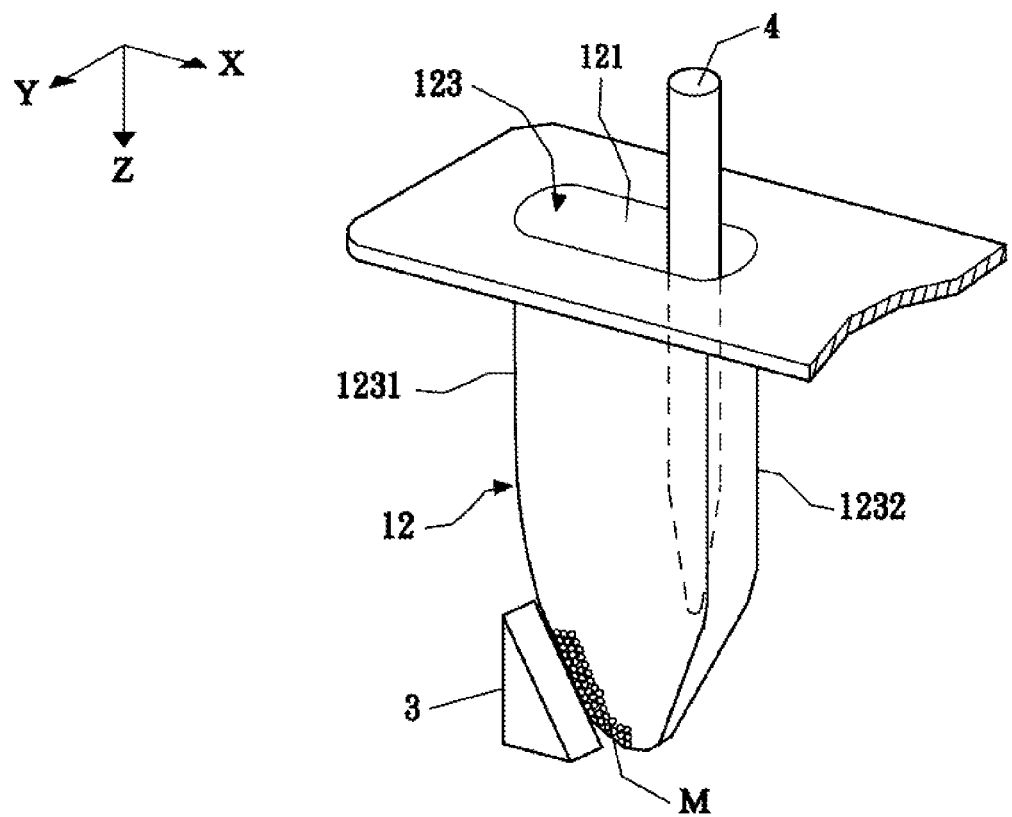
FIG. 1G is a perspective view illustrating how the separation container shown in FIG. 1B is used.

FIG. 1G shows how the separation container 12 of the integral-type reaction cartridge 1 in the first preferred embodiment of the present invention is used. A magnetic field 3 is placed beside the first side 1231 and adjacent to the second end 122. Consequently, magnetic particles M bound with a target substance are attracted by the magnetic field 3 and gather on the first side 1231 in an area near the second end 122. As the first side 1231 of the accommodating space 123 has a pointed configuration near the second end 122, the magnetic particles M form a strip along the first side 1231 in the area near the second end 122. Therefore, when a drawing mechanism 4 is subsequently placed in the accommodating space 123 to draw out the liquid therein, the suction force and vortex that take place during the drawing process are unlikely to disturb the target substance-bound magnetic particles M and cause the magnetic particles M to float in the liquid again. Thus, the target substance-bound magnetic particles M are prevented from being drawn out mistakenly by the drawing mechanism 4. Under such circumstances, the time for which or the suction force with which the drawing mechanism 4 draws the liquid out of the separation container 12 can be increased so as to draw out the liquid completely. This is because the liquid left in the separation container 12 may lower the yield of purification or even lead to failure of purification.

Referring again to FIG. 1B, the opening at the first end 121 of the separation container 12 has a width Wx along the first direction X and a width Wy along the second direction Y. The width Wx is preferably greater than the width Wy.

In the second preferred embodiment of the present invention, an integral-type reaction cartridge is so configured that the number of reaction containers, the material used, and the arrangement of the reaction containers and separation containers are substantially the same as those in the first preferred embodiment and therefore are not repeated herein. However, the second preferred embodiment is different from the first preferred embodiment in the following manner.

Figure 2A:
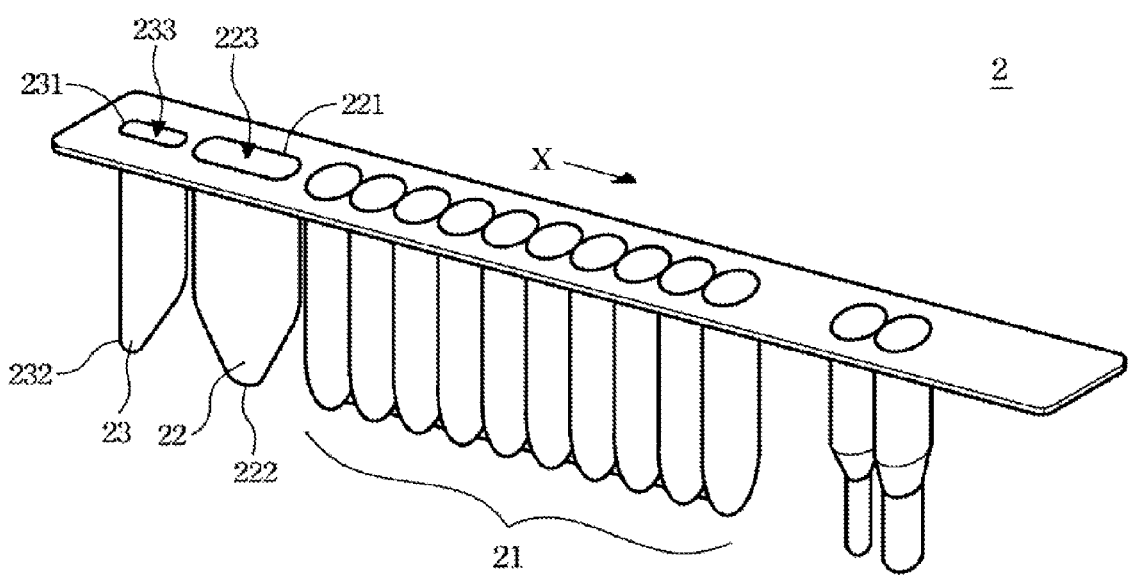
FIG. 2A is a perspective view of an integral-type reaction cartridge according to a second preferred embodiment of the present invention.

Referring to FIG. 2A, an integral-type reaction cartridge 2 according to the second preferred embodiment of the present invention includes a plurality of reaction containers 21, a first separation container 22, and a second separation container 23. The reaction containers 21, the first separation container 22, and the second separation container 23 are integrally formed of plastic and lined along a first direction X.

Figure 2B:
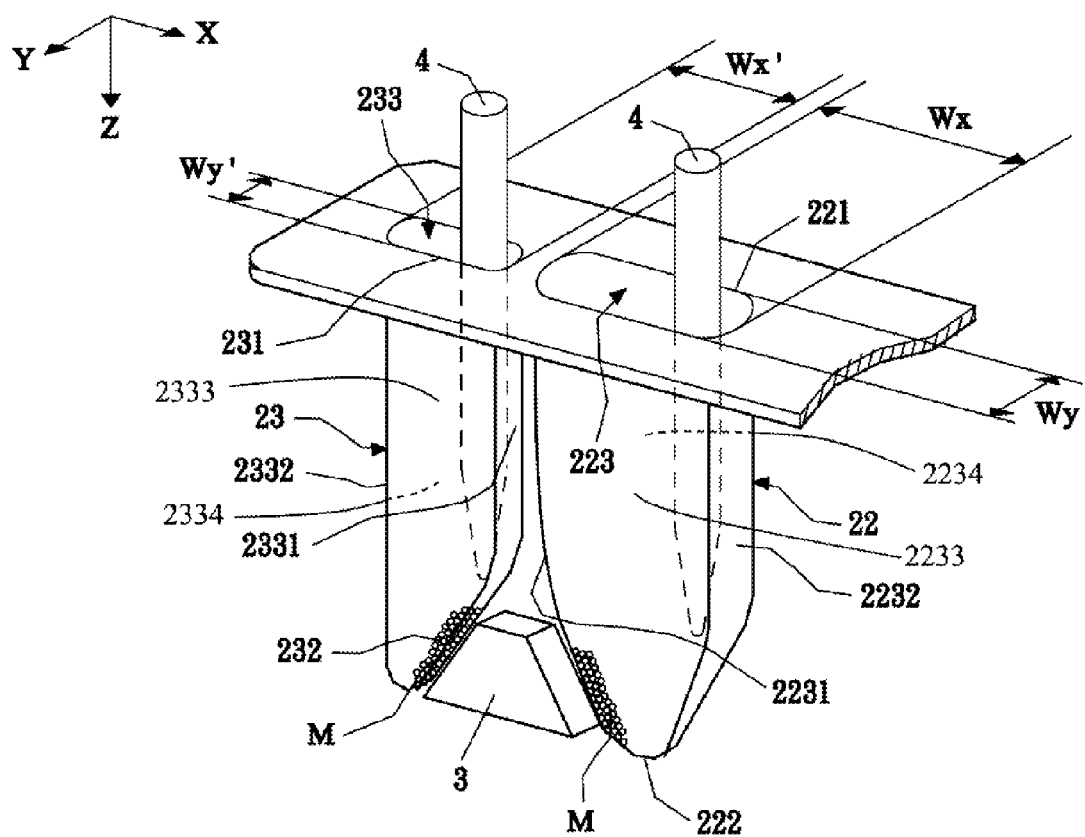
FIG. 2B is a perspective view of a first separation container and a second separation container of the integral-type reaction cartridge shown in FIG. 2A.

As shown in FIG. 2B, the first separation container 22 and the second separation container 23 are adjacent to each other. Like the separation container 12 in the first preferred embodiment, the first separation container 22 has a first end 221, a second end 222 opposing the first end 221, and a hollow accommodating space 223 between the first end 221 and the second end 222, wherein the first end 221 is an open end, and the second end 222 is a closed end. The accommodating space 223 of the first separation container 22 has a first side 2231 and a second side 2232 along the first direction X, as well as a third side 2233 and a fourth side 2234 along a second direction Y, wherein the second direction Y is perpendicular to the first direction X. The relative positions and configuration features of the first through fourth sides 2231, 2232, 2233, 2234 are the same as those of the first through fourth sides 1231, 1232, 1233, 1234 in the first preferred embodiment and hence are not described repeatedly.

The second separation container 23 also has a first end 231, a second end 222 opposing the first end 231, and a hollow accommodating space 233 between the first end 231 and the second end 232, wherein the first end 231 is an open end, and the second end 232 is a closed end.

The accommodating space 233 of the second separation container 23 has a fifth side 2331 and a sixth side 2332 along the first direction X, as well as a seventh side 2333 and an eighth side 2334 along the second direction Y, which is perpendicular to the first direction X. The fifth side 2331 is adjacent to the first side 2231 of the first separation container 22 and curves toward the center of the accommodating space 233.

The present embodiment is different from the first preferred embodiment in that, near the second end 222 of the first separation container 22, the first side 2231 of the first separation container 22 has a greater slope than either side of the first separation container 22 that is located along the second direction Y (i.e., the third side 2233 or the fourth side 2234); moreover, near the second end 232 of the second separation container 23, the fifth side 2331 adjacent to the first separation container 22 has a greater slope than either side of the second separation container 23 that is located along the second direction Y (i.e., the seventh side 2333 or the eighth side 2334)

To use the first and second separation containers 22, 23, a magnetic field 3 is placed beside the first side 2231 of the first separation container 22 and adjacent to the second end 222 such that magnetic particles M bound with a target substance are attracted by the magnetic field 3 and gather on the first side 2231 in an area near the second end 222. As the first side 2231 of the accommodating space 223 of the first separation container 22 has a pointed configuration near the second end 222, the magnetic particles M form a strip along the first side 2231 in the area near the second end 222. Therefore, when a drawing mechanism 4 is subsequently placed in the accommodating space 223 to draw out the liquid therein, the suction force and vortex generated during the drawing process are unlikely to disturb the target substance-bound magnetic particles M and cause the magnetic particles M to float again in the liquid. In consequence, the target substance-bound magnetic particles M are prevented from being drawn out mistakenly by the drawing mechanism 4. Similarly, the magnetic field 3 is placed beside the fifth side 2331 of the second separation container 23 and adjacent to the second end 232 such that magnetic particles M are attracted by the magnetic field 3 and gather on the fifth side 2331 in an area near the second end 232. As the fifth side 2231 of the accommodating space 233 of the second separation container 23 has a pointed configuration near the second end 232, the magnetic particles M form a strip along the fifth side 2231 in the area near the second end 232. Therefore, when a drawing mechanism 4 is subsequently placed in the accommodating space 233 to draw out the liquid therein, the suction force and vortex generated during the drawing process are unlikely to disturb the target substance-bound magnetic particles M and cause the magnetic particles M to float in the liquid again. As a result, the target substance-bound magnetic particles M are prevented from being drawn out mistakenly by the drawing mechanism 4.

With the foregoing arrangement, the time for which or the suction force with which the drawing mechanism 4 draws the liquid out of the first separation container 22 or the second separation container 23 can be increased so as to draw out the liquid completely, for the liquid left in the first separation container 22 or the second separation container 23 may lower the yield of purification or even lead to failure of purification.

Referring again to FIG. 2B, the opening at the first end 221 of the first separation container 22 has a width Wx along the first direction X and a width Wy along the second direction Y, wherein the width Wx is preferably greater than the width Wy. Meanwhile, the opening at the first end 231 of the second separation container 23 has a width Wx' along the first direction X and a width Wy' along the second direction Y, wherein the width Wx' is preferably greater than the width Wy'.

The preferred embodiments described above serve to demonstrate the features of the present invention so that a person skilled in the art can understand the contents disclosed herein and implement the present invention accordingly. The embodiments, however, are not intended to limit the scope of the present invention. Therefore, all equivalent changes or modifications which do not depart from the spirit of the present invention should fall within the scope of the present invention, which is defined only by the appended claims.

What is claimed is:

1. An integral-type reaction cartridge used in magnetic separation of the process of purifying biomolecules, comprising: a plurality of reaction containers and at least one separation container, the integral-type reaction cartridge being characterized in that:
   the reaction containers and the at least one separation container are integrally formed of plastic and lined along a first direction, the at least one separation container having a first end, a second end opposing the first end, and a hollow accommodating space between the first end and the second end, wherein the first end is an open end, the second end is a closed end, and the accommodating space tapers from the first end to the second end, the accommodating space having a first side and a second side along the first direction, the accommodating space further having a third side and a fourth side along a second direction perpendicular to the first direction, wherein near the second end of the at least one separation container, at least one of the first side and the second side of the accommodating space has a lesser slope than the third side and the fourth side of the accommodating space; the first end of the at least one separation container is formed with an opening with a width along the first direction being greater than a width along the second direction; and the first side is changed from a curved configuration near the first end to a pointed configuration near the second end.

2. The integral-type reaction cartridge of claim 1, wherein near the second end of the at least one separation container, both the first side and the second side of the accommodating space have lesser slopes than the third side and the fourth side of the accommodating space.

3. An integral-type reaction cartridge used in magnetic separation of the process of purifying biomolecules, comprising: a plurality of reaction containers, a first separation container, and a second separation container, the integral-type reaction cartridge being characterized in that:
   the reaction containers, the first separation container, and the second separation container are integrally formed of plastic and lined along a first direction, wherein the first separation container and the second separation container are adjacent to each other, the first separation container and the second separation container respectively has an open end, a closed end opposing the open end, and a hollow accommodating space formed between the open end and the closed end and tapering from the open end to the closed end, the accommodating space has a first side and a second side along the first direction with the first side of the accommodating space of the first separation container being adjacent to the first side of the accommodating space of the second separation container, and the accommodating space further has a third side and a fourth side along a second direction perpendicular to the first direction; wherein near the closed end of the first separation container, the first side and the second side of the accommodating space of the first separation container has a lesser slope than the third side and the fourth side of the accommodating space of the first separation container; wherein near the closed end of the accommodating space of the second separation container, the first side and the second side of the accommodating space of the second separation container has a lesser slope than the third side and the fourth side of the accommodating space of the second separation container; wherein the open end of each separation container is formed with an opening with a width along the first direction being greater than a width along the second direction; and wherein the first side of each separation container is changed from a curved configuration near the open end of each separation container to a pointed configuration near the closed end of each separation container.

* * * * *